United States Patent [19]

Greco et al.

[11] Patent Number: 5,066,656
[45] Date of Patent: Nov. 19, 1991

[54] PHARMACOLOGICALLY ACTIVE (6,7-DIHYDRO-5H-PYRROLO[1,2-C]IMIDAZOL-5-YL)- AND (5,6,7,8-TETRAHYDROIMIDAZO[1,5-A]PYRIDIN-5-YL) SUBSTITUTED 1H-BENZOTRIAZOLE DERIVATIVES

[75] Inventors: Michael N. Greco, Lansdale, Pa.; Marcel A. C. Janssen, Vosselaar, Belgium

[73] Assignee: Janssen Pharmaceutica N.V., Beerse, Belgium

[21] Appl. No.: 580,393

[22] Filed: Sep. 10, 1990

Related U.S. Application Data

[63] Continuation-in-part of Ser. No. 430,030, Nov. 1, 1989, abandoned.

[51] Int. Cl.$^5$ .............. A61K 31/435; A61K 31/415; C07D 471/04; C07D 487/04
[52] U.S. Cl. .................. 514/269; 514/274; 514/300; 514/322; 514/338; 514/359; 514/378; 514/387; 514/393; 544/316; 544/319; 546/121; 546/199; 546/271; 548/247; 548/257; 548/259; 548/260; 548/261
[58] Field of Search ............... 544/316, 319; 546/121, 546/199, 271; 548/247, 257, 259, 260, 261; 514/269, 274, 300, 322, 338, 359, 378, 387, 393

[56] References Cited

U.S. PATENT DOCUMENTS 4,617,307 10/1986 Browne .................. 514/300
4,755,526 7/1988 Hirsch et al. .............. 514/399

FOREIGN PATENT DOCUMENTS

EP-A-0
293978 12/1988 European Pat. Off. .

Primary Examiner—Bernard Dentz
Attorney, Agent, or Firm—Charles J. Metz

[57] ABSTRACT (6,7-dihydro-5H-pyrrolo[1,2-c]imidazolyl-5-yl)- and (5,6,7,8-tetrahydroimidazo[1,5-a]pyridinyl-5-yl) substituted 1H-benzotriazole derivatives, compositions containing the same and methods of treating estrogen dependent disorders.

9 Claims, No Drawings

PHARMACOLOGICALLY ACTIVE (6,7-DIHYDRO-5H-PYRROLO[1,2-C]IMIDAZOL-5-YL)- AND (5,6,7,8-TETRAHYDROIMIDAZO[1,5-A]PYRIDIN-5-YL) SUBSTITUTED 1H-BENZOTRIAZOLE DERIVATIVES

CROSS-REFERENCE TO RELATED APPLICATION

This is a continuation-in-part of our copending application Ser. No. 430,030 filed Nov. 1, 1989, now abandoned.

BACKGROUND OF THE INVENTION

In U.S. Pat. No. 4,617,307 there are described aryl substituted imidazo [1,5-a]pyridines and the corresponding 7,8-dihydro- and 5,6,7,8-tetrahydro-derivatives thereof for use as inhibitors of the enzyme aromatase.

In EP-A-0,293,978 there are described (1H-azol-1-ylmethyl)substituted benzotriazole derivatives as aromatase inhibitors useful in combatting estrogen dependent disorders.

DESCRIPTION OF THE INVENTION

The present invention is concerned with benzotriazole derivatives having the formula

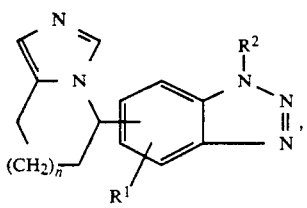

(I)

the pharmaceutically acceptable acid addition salts thereof and the stereochemically isomeric forms thereof, wherein n is 0 or 1;

$R^1$ is hydrogen, nitro, amino, mono- or di($C_{1-6}$alkyl)amino, halo, $C_{1-6}$alkyl, hydroxy or $C_{1-6}$alkyloxy;

$R^2$ is hydrogen; $C_{1-10}$alkyl; $C_{3-6}$alkenyl; $C_{3-6}$alkynyl; $C_{3-7}$cycloalkyl; bicyclo[2.2.1]heptan-2-yl; 2,3-dihydro-1H-indenyl; 1,2,3,4-tetrahydronaphthalenyl; phenyl; substituted phenyl; $C_{1-10}$alkyl substituted with phenyl, substituted phenyl, naphthalenyl, thienyl, furanyl, $C_{1-4}$alkylfuranyl, $C_{3-7}$cycloalkyl, hydroxy or with $C_{1-6}$alkyloxy; or a radical of formula $—OR^3$;

$R^3$ is hydrogen; $C_{1-10}$alkyl; $C_{3-6}$alkenyl; phenyl$C_{3-6}$alkenyl; $C_{3-6}$alkynyl; pyrimidinyl; diphenylmethyl; 1-$C_{1-4}$alkylpiperidin-4-yl; $C_{1-10}$alkyl substituted with halo, hydroxy, $C_{1-6}$alkyloxy, amino, mono- or di($C_{1-4}$alkyl)amino, trifluoromethyl, cyano, aminocarbonyl, hydroxycarbonyl, $C_{1-6}$alkyloxycarbonyl, phenyl, substituted phenyl, thienyl, furanyl, $C_{1-4}$alkylfuranyl, pyridinyl, di($C_{1-6}$alkyl)isoxazolyl, phenoxy, phenylthio, $C_{3-7}$cycloalkyl, 2,3-dihydro-1,4-benzodioxinyl, 1H-benzimidazolyl, $C_{1-4}$alkyl substituted 1H-benzimidazolyl, (1,1'-biphenyl)-4-yl or 2,3-dihydro-2-oxo-1H-benzimidazolyl; and each substituted phenyl independently is phenyl substituted with from 1 to 3 substituents independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro.

As used in the foregoing definitions the term halo is generic to fluoro, chloro, bromo and iodo; the term "$C_{1-4}$alkyl" defines straight and branch chained saturated hydrocarbon radicals having from 1 to 4 carbon atoms such as, for example, methyl, ethyl, 1-methylethyl, 1,1-dimethylethyl, propyl, 2-methylpropyl, butyl and the like; the term "$C_{1-6}$alkyl" defines $C_{1-4}$alkyl radicals as defined hereinabove and the higher homologs thereof having 5 or 6 carbon atoms such as, for example, pentyl, hexyl and the like; "$C_{1-10}$alkyl defines $C_{1-6}$alkyl radicals as defined hereinabove, and the higher homologs thereof having from 7 to 10 carbon atoms such as, for example, heptyl, octyl, nonyl, decyl and the like; the term "$C_{3-7}$cycloalkyl" defines cyclopropyl, cyclobutyl, cyclopentyl, cyclohexyl and cycloheptyl. "$C_{3-6}$alkenyl" defines straight and branch chained hydrocarbon radicals containing one double bond and having from 3 to 6 carbon atoms such as, for example, 2-propenyl, 2-methyl-2-propenyl, 3-butenyl, 2-butenyl, 2-pentenyl, 3-pentenyl, 3-methyl-2-butenyl and the like; "$C_{3-6}$alkynyl" defines straight and branch chained hydrocarbon radicals containing one triple bond and having from 3 to 6 carbon atoms such as, for example, 2-propynyl, 2-butynyl, 3-butynyl, 2-pentynyl, 4-pentynyl and the like; and when a $C_{3-6}$alkenyl or a $C_{3-6}$alkynyl is substituted on a heteroatom, then the carbon atom of said $C_{3-6}$alkenyl or said $C_{3-6}$alkynyl connected to said heteroatom preferably is saturated.

The 5,6,7,8-tetrahydroimidazo[1,5-a]pyridin-5-yl (n=1) or 6,7-dihydro-5H-pyrrolo[1,2-c]imidazol-5-yl (n=0) moiety of formula

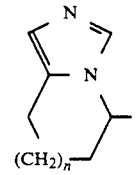

in the compounds of formula (I) as defined hereinabove, may be substituted on any of the 4, 5, 6 or 7 positions of the benzotriazole moiety.

The compounds of formula (I) and some of the intermediates in this invention have an asymmetric carbon atom in their structure. This chiral center may be present in a R- and a S-configuration, this R- and S-notation being in correspondence with the rules described in Pure Appl. Chem., 1976, 45, 11-30.

The acid addition salts as mentioned hereinabove are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term acid addition salt also comprises the hydrates and solvent addition forms which the compounds of formula (I) are able to form. Examples of such forms are e.g. hydrates, alcoholates and the like.

A first particular subgroup among the compounds of formula (I) comprises those compounds of formula (I) wherein n is 1.

A second particular subgroup among the compounds of formula (I) comprises those compounds of formula (I) wherein n is 0.

A third particular subgroup among the compounds of formula (I) comprises those compounds of formula (I) wherein $R^2$ is hydrogen; $C_{1-10}$alkyl; $C_{3-6}$alkenyl; $C_{3-6}$alkynyl; $C_{3-7}$cycloalkyl; bicyclo[2.2.1]heptan-2-yl; 2,3-dihydro-1H-indenyl; 1,2,3,4-tetrahydronaphthalenyl; phenyl; substituted phenyl; $C_{1-10}$alkyl substituted with phenyl, substituted phenyl, naphthalenyl, thienyl, furanyl, $C_{1-4}$alkylfuranyl, $C_{3-7}$cycloalkyl, hydroxy or $C_{1-6}$alkyloxy.

A fourth particular subgroup among the compounds of formula (I) comprises those compounds of formula (I) wherein $R^2$ is a radical of formula $OR^3$.

Particular compounds are those compounds of formula (I) wherein the 5,6,7,8-tetrahydroimidazo[1,5-a]pyridin-5-yl or the 6,7-dihydro-5H-pyrrolo[1,2-c]imidazol-5-yl moiety is substituted on either the 5 or the 6 position of the benzotriazole moiety.

More particular compounds are those particular compounds wherein n is 1; and/or $R^1$ is hydrogen; and/or $R^2$ is hydrogen, $C_{1-6}$alkyl, $C_{3-6}$alkenyl, $C_{3-6}$alkynyl, $C_{3-7}$cycloalkyl, phenyl, substituted phenyl, bicyclo[2.2.1]heptan-2-yl, 2,3-dihydro-1H-indenyl, 1,2,3,4-tetrahydronaphthalenyl, $C_{1-6}$alkyl substituted with phenyl, substituted phenyl, naphthalenyl, thienyl, furanyl, $C_{1-4}$alkylfuranyl, $C_{3-7}$cycloalkyl, hydroxy, $C_{1-4}$alkyloxy or a radical —$OR^3$; and;

$R^3$ is hydrogen, $C_{1-6}$alkyl, $C_{3-6}$alkenyl, phenyl$C_{3-6}$alkenyl; $C_{3-6}$alkynyl; pyrimidinyl; diphenylmethyl, (1-$C_{1-4}$alkyl-4-piperidinyl); $C_{1-6}$alkyl substituted with halo, hydroxy, amino, mono- or di($C_{1-6}$alkyl)amino, trifluoromethyl, cyano, aminocarbonyl, hydroxycarbonyl, $C_{1-6}$alkyloxycarbonyl, phenyl, substituted phenyl, thienyl, furanyl, $C_{1-4}$alkylfuranyl, pyridinyl, di($C_{1-6}$alkyl)isoxazolyl, phenoxy, phenylthio, $C_{3-7}$cycloalkyl, 2,3-dihydro-1,4-benzodioxinyl, 1H-benzimidazolyl, $C_{1-4}$alkyl substituted 1H-benzimidazolyl, (1,1'-biphenyl)-4-yl or 2,3-dihydro-2oxo-1H-benzimidazolyl.

Other more particular compounds are those particular compounds wherein n is 0; and/or $R^1$ is hydrogen; and/or $R^2$ is hydrogen, $C_{1-6}$alkyl, $C_{3-7}$cycloalkyl, $C_{1-6}$alkyl substituted with $C_{3-7}$cycloalkyl, or a radical —$OR^3$; and $R^3$ is hydrogen or $C_{1-6}$alkyl.

Preferred compounds are those more particular compounds wherein n is 1; and/or $R_2$ is $C_{1-6}$alkyl optionally substituted with $C_{3-7}$cycloalkyl; $C_{3-7}$cycloalkyl; bicyclo[2.2.1]heptan-2-yl; 2,3-dihydro-1H-indenyl; 1,2,3,4-tetrahydronaphthalenyl; or a radical —$OR^3$; and $R^3$ is $C_{1-6}$alkyl optionally substituted with hydroxy, cyano, phenyl, substituted phenyl, $C_{3-7}$cycloalkyl; or $C_{3-6}$alkenyl.

Especially preferred compounds are those preferred compounds wherein $R^2$ is $C_{1-4}$ alkyl.

The most preferred compounds within the present invention are selected from the group comprising 1-ethyl-6-(5,6,7,8-tetrahydroimidazo[1,5-a]pyridin-5-yl)-1H-benzotriazole monohydrochloride, the free base, the other pharmaceutically acceptable acid addition salt forms thereof and the stereochemically isomeric forms thereof.

The compounds of formula (I) wherein $R^2$ is other than $OR^3$, said compounds being represented by formula (I-a) and said radical by $R^{2-a}$, can generally be prepared from an appropriate aromatic diamine of formula (II) by reaction with a suitable diazotizing reagent.

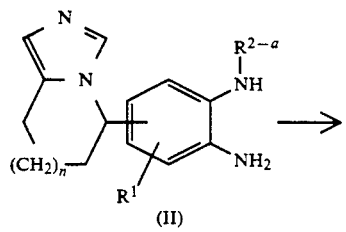

(II)

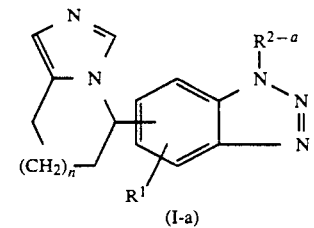

(I-a)

Suitable diazotizing reagents are alkylnitrites, e.g. 1,1-dimethylethylnitrite, isoamylnitrite and the like; nitronium tetrafluoroborate, nitrous acid in aqueous solution, or more particularly aqueous solutions of nitrite salts such as, for example, sodium nitrite, potassium nitrite, silver nitrite and the like, in the presence of a mineral and/or organic acid such as, for example, hydrohalic acids, e.g. hydrochloric, hydrobromic and the like acids; perchloric acid, perbromic acid, periodic acid, phosphoric acid, sulfuric acid, nitric acid and the like; carboxylic acids, e.g. formic, acetic, trifluoroacetic, propanoic, benzoic, methanesulfonic and the like acids.

Said reaction can conveniently be conducted by stirring the aromatic diamine of formula (II) in the presence of a suitable diazotizing reagent as defined hereinabove, at a low temperature, in an aqueous solution, optionally in admixture with organic cosolvents such as, for example, alkanols, e.g. methanol, ethanol and the like.

The compounds of formula (I) wherein $R^3$ is other than hydrogen, said compounds being represented by formula (I-b) and said radical by $R^{3-a}$, can generally be prepared by O-alkylating a compound of formula (I) wherein $R^3$ is hydrogen, said compounds being represented by formula (I-c), with an appropriate alkylating reagent of formula $R^{3-a}$-W (III).

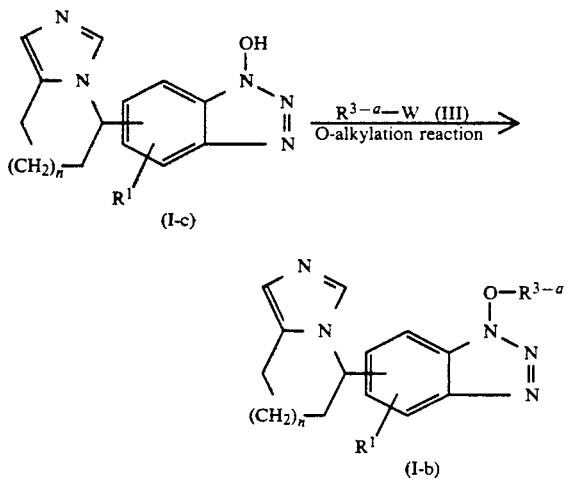

In formula (III) and hereinafter W represents an appropriate reactive leaving group such as, for example, halo, e.g. chloro, bromo, iodo, or a sulfonyloxy group, e.g. 4-methylbenzenesulfonyloxy, benzenesulfonyloxy, 2-naphthalenesulfonyloxy, methanesulfonyloxy, trifluoromethanesulfonyloxy and the like reactive leaving groups.

Said O-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 4-methyl-2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, an amine, e.g. N,N-diethylethanamine, N-(1-methylethyl)-2-propanamine, 4-ethylmorpholine, 1,4-diazabicyclo[2.2.2]octane, pyridine and the like, may optionally be used to pick up the acid which is formed during the course of the reaction. Further, it may be advantageous to convert the compound (I-c) first into a suitable salt form thereof such as, for example, an alkali or earth alkaline metal salt, by reacting (I-c) with an appropriate base as defined hereinabove and subsequently using said salt form in the reaction with the alkylating reagent of formula (III). In some instances the addition of an iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said O-alkylation under an inert atmosphere such as, for example, oxygen-free argon or nitrogen gas. Alternatively, said O-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraallkylphosphonium, tetraarylphosphonium halide, hydroxide, hydrogen sulfate and the like catalysts. Somewhat elevated temperatures may be appropriate to enhance the rate of the reaction.

The compounds of formula (I-c) in turn can be prepared by cyclizing an appropriately substituted nitrobenzene derivative of formula (IV) wherein $W^1$ represents a reactive leaving group, with hydrazine, a hydrate thereof or an acid addition salt thereof.

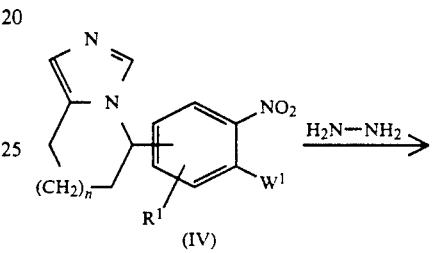

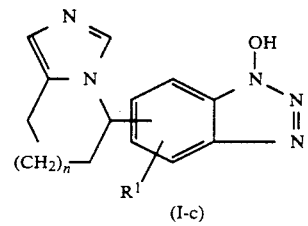

The reactive leaving group $W^1$ represents groups such as, for example, halo, e.g. chloro, bromo or preferably fluoro, nitro, sulfonyloxy groups, e.g. methanesulfonyloxy, 4-methylbenzenesulfonyloxy and the like, aryloxy, $C_{1-6}$alkyloxy or $C_{1-6}$alkylthio and the like groups. Said cyclization may be carried out by stirring the reactants in a reaction-inert solvent such as, for example, an alkanol, e.g. methanol, ethanol, 2-propanol, 1-butanol and the like, an aromatic hydrocarbon, e.g. benzene, methylbenzene, dimethylbenzene and the like, or a mixture of such solvents. Somewhat elevated temperatures may be appropriate to enhance the rate of the reaction and preferably the reaction is carried out at the reflux temperature of the reaction mixture.

The compounds of formula (I-a) wherein $R^{2-a}$ is hydrogen, said compounds being represented by formula (I-a-1) may also be prepared from the compounds of formula (I-c) following art-known reduction procedures.

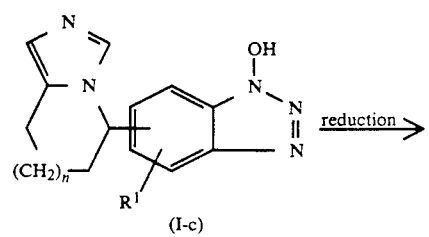

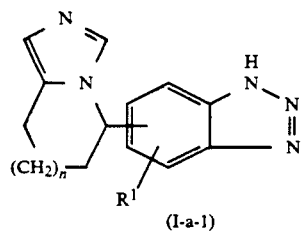

(I-a-1)

Said reduction may be conducted, for example, by catalytic hydrogenation in the presence of hydrogen and an appropriate hydrogenation catalyst such as, for example, platinum, palladium, platinum(IV) oxide, Raney-nickel and the like, in the presence of a reaction inert organic solvent such as, for example, an alkanol, e.g. methanol, ethanol, 2-propanol, butanol and the like.

Said reduction may alternatively be conducted by reducing the starting material with a reducing agent such as, for example, titanium(III)chloride or tin(II)chloride in hydrochloric acid, optionally in the presence of a reaction-inert solvent. Preferably said reduction is carried out by converting the hydroxy group into a readily leaving group, such as, for example, an ether —O—CH$_2$—Z wherein Z is an electronwithdrawing group such as cyano, C$_{1-6}$alkyloxycarbonyl, aminocarbonyl, mono- or di(C$_{1-6}$alkyl)aminocarbonyl and the like, by reaction with an O-alkylating reagent of formula W—CH$_2$—Z, and stirring the thus obtained ether intermediates in the presence of a base such as, for example, an alkali or earth alkaline metal carbonate, hydrogen carbonate, hydroxide, alkoxide or amide, in an appropriate solvent such as, for example, a dipolar aprotic solvent, e.g. dimethyl sulfoxide, N,N-dimethylformamide and the like solvents, thus eliminating OHC-Z and yielding the desired benzotriazole of formula (I-a-1). Said O-alkylation and elimination can easily be conducted in a one-pot procedure.

The compounds of formula (I) wherein R$^2$ is other than hydrogen and OR$^3$, said compounds being represented by formula (I-a-2) and said radical by R$^{2-b}$, may be prepared by N-alkylating a compound of formula (I-a-1) with a reagent of formula R$^{2-b}$-W, wherein W is a leaving group as defined hereinabove.

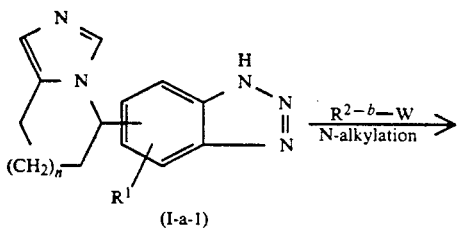

(I-a-1)

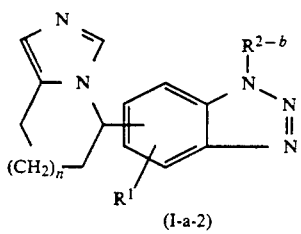

(I-a-2)

Said N-alkylation reaction of (I-a-1) may conveniently be conducted following the procedures described here-inabove for the preparation of the compounds of formula (I-b) from the compounds of formula (I-c).

The compounds of formula (I) may also generally be prepared by cyclizing an intermediate of formula (V) wherein W is a reactive leaving group as defined hereinabove in a suitable reaction inert solvent in the presence of an appropriate base.

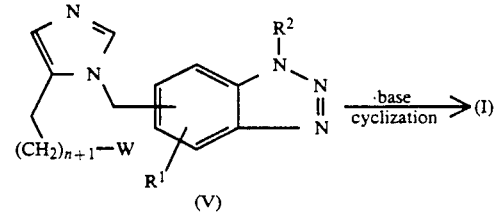

(V)

Appropriate bases are, for example, alkali and earth alkaline metal hydroxides and oxides, e.g. sodium hydroxide, potassium hydroxide and the like, sodium hydride, organic amines, e.g. N-(1-methylethyl)-2-propanamine, N,N-diethylethanamine, 1,8-diazabicyclo[5.4.0]undec-7-ene, lithium salts of secondary amines, e.g. lithium diisopropylamide and the like. Suitable solvents are, for example, ethers, e.g. 1,1'-oxybisethane, tetrahydrofuran, 1,4-dioxane and the like, dipolar aprotic solvents, e.g. N,N-dimethylformamide, N,N-dimethylacetamide, dimethylsulfoxide and the like, and mixture of such solvents, optionally in admixture with hydrocarbons, e.g. pentane, hexane and the like. Said cyclization can conveniently be conducted at low to ambient temperature, in particular from about −10° C. to about room temperature, optionally under an inert atmosphere, e.g. argon or nitrogen.

Alternatively the compounds of formula (I) may also be prepared by cyclizing an intermediate of formula (VI) wherein P is either hydrogen or a protective group such as, for example, a trialkylsilyl group, e.g. trimethylsilyl, triethylsilyl or tert. butyldimethylsilyl, an acyl group, e.g. acetyl, propanoyl and the like, a carbamoyl group, e.g. dimethylaminocarbonyl, or a triphenylmethyl group; and W is a leaving group as defined hereinabove.

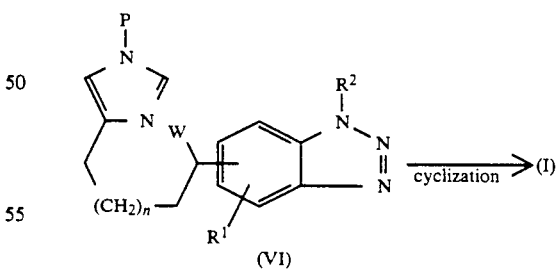

(VI)

Said cyclization reaction may conveniently be conducted by stirring the intermediate (VI) in a reaction-inert solvent, optionally in the presence of a base such as, for example, an organic amine, e.g. N,N-diethylethanamine and the like, and optionally heating the reaction mixture.

The compounds of formula (I) may also be prepared by condensing an aldehyde of formula (VII) in the presence of a base at an enhanced temperature and subsequently reducing the thus obtained enamine (VIII).

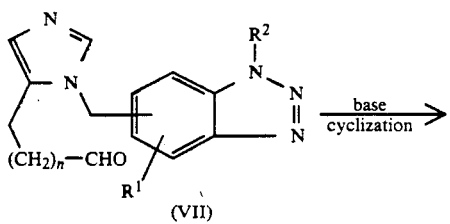

(VII)

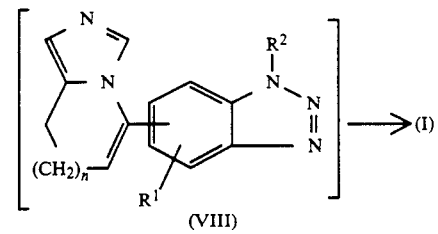

(VIII)

Said reductive amination can conveniently be carried out by reacting the intermediate (IX) with an appropriate reducing agent such as, for example, hydrogen in the presence of a hydrogenation catalyst, e.g. palladium-on-charcoal, platinum-on-charcoal, Raney nickel and the like or an hydride donor, e.g. sodium cyanoborohydride and the like reductants. Said reduction may also be conducted in a two step fashion by first generating the enamine (VIII) from intermediate (IX) by treatment with an appropriate acid catalyst such as, for example, methylbenzenesulfonate and the like, and subsequently reducing said enamine as described hereinabove.

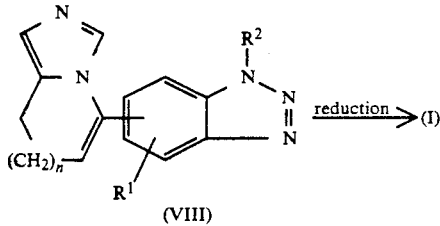

(VIII)

Said cyclization can be carried out by reacting the intermediate (VII) with a base such as, for example, an alkali or earth alkaline metal hydroxide or oxide, e.g. sodium hydroxide, potassium hydroxide and the like, an organic amine, e.g. N,N-diethylethanamine, 1,8-diazabicyclo[5.4.0]undec-7-ene, pyridine and the like, in a reaction-inert solvent such as, for example, an alcohol, e.g. methanol, ethanol, 2-propanol, 1-butanol and the like, a ketone, e.g. acetone, 4-methyl-2-pentanone and the like, an ether, e.g. 1,1'-oxybisethane, tetrahydrofuran, 1,4-dioxane and the like, an aromatic hydrocarbon, e.g. benzene, methylbenzene and the like, a halogenated hydrocarbon e.g. dichloromethane, trichloromethane and the like, a dipolar aprotic solvent, e.g. N,N-dimethylformamide, N,N-dimethylacetamide, dimethylsulfoxide and the like or a mixture of such solvents. The thus obtained intermediate (VIII) may be reduced following art-known reduction procedures, e.g. by catalytic hydrogenation in the presence of hydrogen and an appropriate hydrogenation catalyst, e.g. palladium-on-charcoal, platinum-on-charcoal, Raney-nickel and the like in a reaction-inert solvent such as, for example, an alkanol, e.g. ethanol or an ester, e.g. ethyl acetate and the like solvents, optionally at an increased pressure and/or temperature; or by reaction with a reducing agent such as, for example, sodium borohydride, sodium cyanoborohydride and the like.

Alternatively, the compounds of formula (I) may also be prepared by reductively aminating an intermediate of formula (IX).

The compounds of formula (I) may further also be converted into each other following art-known functional group transformation procedures. A number of such procedures will be described hereinafter in more detail. The compounds of formula (I) containing a cyano group may be hydrolyzed to the corresponding compounds containing an aminocarbonyl or hydroxycarbonyl group by treatment with an acid and/or a base. Conversely said compounds containing an aminocarbonyl group may be dehydrated to compounds containing a cyano group. The carboxylic acid group may be converted into the corresponding ester or amide groups following art-known esterification and amidation procedures. For example, the carboxylic acid may be converted into a reactive derivative thereof such as, for example, an acyl halide, an acid anhydride and the like, which is subsequently reacted with a suitable alkanol or amine; or by reacting the carboxylic acid and the alkanol or amine with a suitable reagent capable of forming esters and amides, e.g. dicyclohexylcarbodiimide, 2-chloro-1-methylpyridinium chloride and the like reagents. Conversely, the compounds of formula (I) containing an ester group may be converted into the corresponding carboxylic acids following art-known hydrolysis procedures, e.g. by treating the ester with an aqueous alkaline or aqueous acidic solution. The compounds of formula (I) wherein $R^2$ or $R^3$ is $C_{1-10}$alkyl substituted with hydroxy may be O-alkylated with a reagent $C_{1-6}$alkyl-W, wherein W is a reactive leaving group as defined hereinabove following the O-alkylation procedures as described hereinabove. Further, the compounds containing a $C_{1-10}$alkyl group substituted with hydroxy may be converted into compounds wherein said $C_{1-10}$alkyl group is substituted by halo following art-known hydroxy-to-halo conversion reactions, e.g. by treatment with a hydrohalic acid, e.g. hydrochloric, hydrobromic and the like acids, thionylchloride, phosphor trichloride and the like halogenating reagents. The thus obtained compounds of formula (I) containing a $C_{1-10}$alkyl group substituted with halo can further be reacted with a nucleophile such as, for example, cyanide, an amine, an alkanol, a phenol or a thiophenol, thus yielding compounds of formula (I) containing a $C_{1-10}$alkyl group substituted with respectively

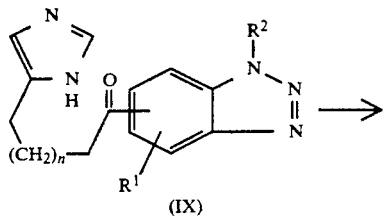

(IX)

cyano, amino, hydroxy, alkyloxy, phenoxy or phenylthio. Compounds of formula (I) containing a formyl group may be converted into the corresponding oxime following art-known procedures, e.g., by treating the starting compound with hydroxylamine or an acid addition salt form thereof in a suitable solvent, e.g., water, a lower alkanol, an ether, in the presence of a base, e.g., an alkali metal hydroxide, carbonate or hydrogen carbonate. Compounds of formula (I) containing an alkynyl group may be converted into the corresponding compounds having an alkenyl or alkyl group by catalytically hydrogenating the starting compound in a suitable reaction-inert solvent according to art-known catalytic hydrogenation procedures. Suitable catalysts are for example palladium-on-charcoal, platinum-on-charcoal and the like. Compounds of formula (I) wherein $R^1$ is hydrogen may be converted into compounds wherein $R^1$ is nitro by stirring the starting compound in a solution of nitric acid in the presence of an appropriate acid, e.g., sulfuric acid, or a mixture of acetic acid and acetic anhydride.

Some of the intermediates and the starting materials in the foregoing are known and may be prepared according to art-known methodologies of preparing said or similar intermediates and starting materials, and a number of intermediates are novel. A number of such preparation methods will be described hereinafter in more detail.

The intermediates of formula (II) can generally be rpepared from the corresponding nitro derivatives of formula (X) by reaction with an appropriate reducing agent.

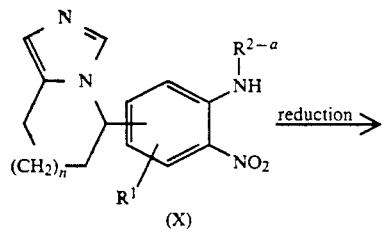

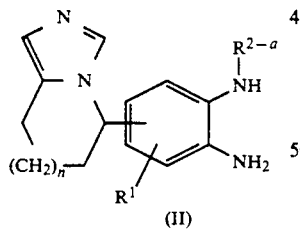

Suitable reducing agents for use in the above nitro-to-amine reduction are, for example, hydrazine in the presence of a catalyst like Raney-nickel; or hydrogen in the presence of an appropriate hydrogenation catalyst such as, for example, palladium-on-charcoal, platinum-on-charcoal, Raney-nickel and the like catalysts. Said reduction can conveniently be conducted in a reaction inert solvent such as, for example, an alkanol, e.g. methanol, ethanol, 2-propanol and the like, optionally at an elevated pressure and/or temperature. Alternatively said reduction can also be conducted by reacting the nitro derivative (X) with a reducing agent such as sodium dithionate in water optionally in admixture with an alkanol, e.g. methanol, ethanol and the like.

The nitro derivative (X) in turn can be prepared from an intermediate (IV) by reaction with a suitable amine of formula (XI).

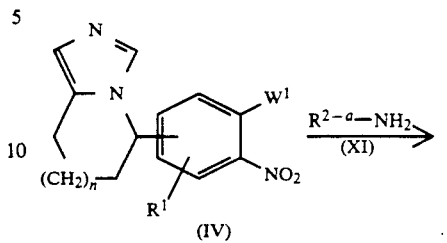

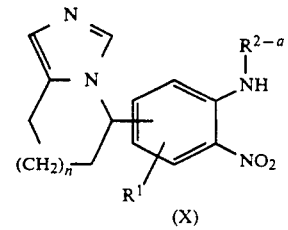

Said reaction can conveniently be conducted by stirring and, if desired, heating the reactants in a reaction-inert solvent such as, for example, an alkanol, e.g. methanol, ethanol, propanol, butanol, 1,2-ethanediol and the like, an ether, e.g. 1,1'-oxybisethane, tetrahydrofuran, 1,4-dioxane and the like, a dipolar aprotic solvent, e.g. N,N-dimethylformamide, dimethylsulfoxide, acetonitrile and the like, a halogenated solvent, e.g. trichloromethane, tetrachloromethane and the like; or a mixture of such solvents. The addition of a suitable base to pick up the acid which is liberated during the reaction may be appropriate; particularly convenient however is the use of an excess of the amine of formula (XI).

The intermediates of formula (IV) can conveniently be prepared by nitration of a benzene derivative of formula (XII) following art-known nitration procedures.

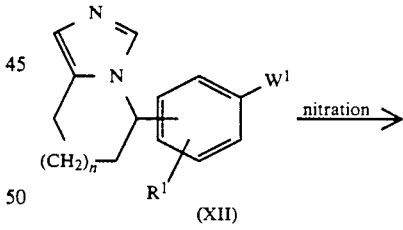

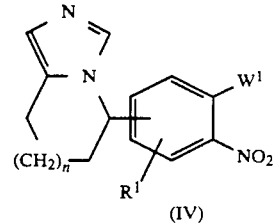

Said nitration reaction is conveniently conducted by treating the intermediate (XII) with nitric acid or the nitrate salt of (XII), in the presence of concentrated sulfuric acid at low or ambient temperature. In some instances it may be appropriate to heat the reactants. Said nitration can be conducted without an additional solvent or may also be performed in a suitable solvent such as, for example, a halogenated hydrocarbon, e.g. trichloromethane, tetrachloromethane and the like, a carboxylic acid or a derivative thereof, e.g. acetic acid, acetic anhydride and the like solvents.

the intermediates of formula (XII) can be obtained from an appropriately substituted 1-phenylmethyl-1H-imidazole of formula (XIII) by converting the hydroxy group to a leaving group W as defined hereinabove and cyclizing the thus obtained intermediate (XIV) by treatment with a suitable base.

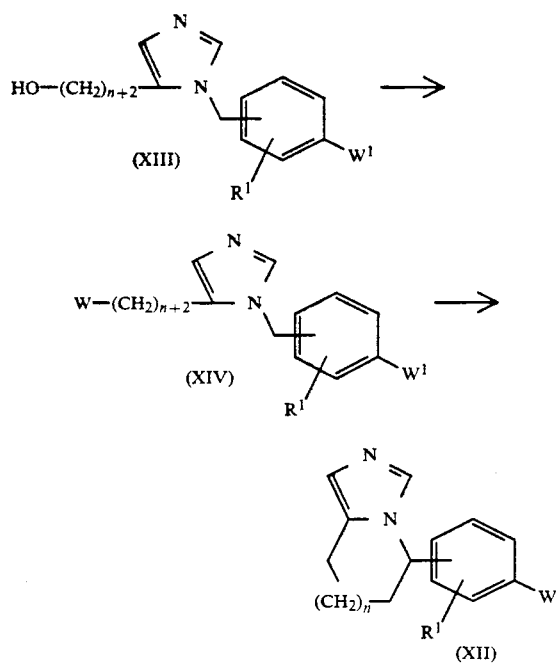

Said cyclization can be conducted by treating the intermediate (XIV) with suitalbe base such as, for example, an alkali or earth alkaline metal hydroxide or oxide, e.g. sodium hydroxide, potassium hydroxide and the like, sodium hydride, organic amines, e.g. N-(1-methylethyl)-2-propanamine, N,N-diethylethanamine, 1,8-diazabicyclo[5,4-0]undec-7-ene, lithium salts of secondary amines, e.g. lithium diisopropylamide, sodium amide and the like bases, in a reaction-inert solvent such as, for example, an ether, e.g. 1,1'-oxybisethane, tetrahydrofuran, 1,4-dioxane and the like, dipolar aprotic solvents, e.g. N,N-dimethylformamide, N,N-dimethylacetamide and the like, and mixtures of such solvents, optionally in admixture with hydrocarbons, e.g. hexane and the like, or amines, e.g. N-(1-methylethyl)-2-propanamine, N,N,N',N'-tetramethyl-1,2-ethanediamine and the like, or mixtures thereof. Said cyclization preferably is conducted at low to ambient temperature.

The intermediates of formula (XIV) can easily be obtained from the intermediates of formula (XIII) by reaction in a reaction-inert solvent with a halogenating reagent such as, for example, hydrohalic acids, e.g. hydrochloric, hydrobromic and the like acids, phosphortrichloride, phosphoryl chloride, thionyl chloride and the like, or a sulfonylating reagent such as, for example, methanesulfonylchloride, benzenesulfonylchloride, 4-methylbenzenesulfonylchloride and the like.

The intermediates of formula (XIII) can be prepared from a methylbenzene derivative (XV) wherein W is a reactive leaving group as defined above, with an appropriately substituted imidazole of formula (XVI), wherein P is a protecting group such as, for example, a trialkylsilylgroup, e.g. trimethylsilyl, triethylsilyl, tert. butyldimethylsilyl and the like, an acyl group, e.g. acetyl, propanoyl and the like, a carbamoyl group, e.g. dimethylaminocarbonyl and the like, or a triphenylmethyl group.

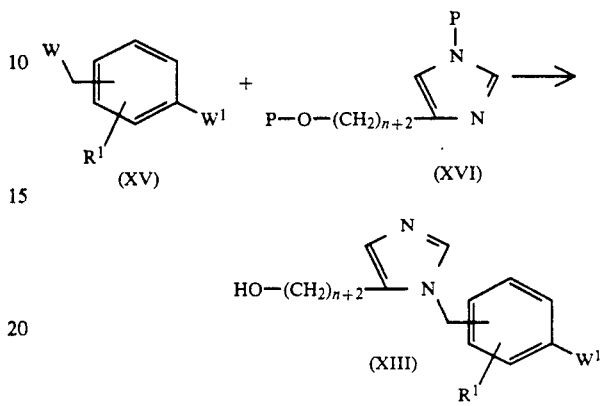

Pure stereochemically isomeric forms of the compounds of this invention may be obtained by the application of art-known procedures. Diastereoisomers may be separated by physical separation methods such as selective crystallization and chromatographic techniques, e.g. counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically. Preferably if a specific stereoisomer is desired said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I), the pharmaceutically acceptable acid-addition salts and possible stereochemically isomeric forms thereof inhibit the action of the enzyme aromatase which catalyses the formation of estrogens from androgenic steroids in mammals.

The inhibition of estrogen formation from androstenedione and testosterone can be demonstrated by in vitro- or in vivo- tests in mammals such as dogs, rats, mice and cats. The in vitro- inhibition of the aromatase activity can, for example, be demonstrated by analyzing the effects of the compounds of the present invention on the conversion of [1,2³H]-androstenedione or [4¹⁴C]-androstenedione into estrone and estradiol in the presence of human placental microsomes. The in vivo- inhibition of the aromatase activity can, for example, be demonstrated by measuring the suppression of the plasma estrogen concentration in female rats. The "In vitro- inhibition of the aromatase activity"-test and the "In vivo- inhibition of the aromatase activity"-test described hereinafter illustrate the estrogen inhibiting properties of the compounds of formula (I) and are based on the above principles. Quite unexpectedly some of the present compounds show an improved in vivo activity over related prior art compounds.

In view of their capability to inhibit the biosynthesis of estrogens the subject compounds can be used in the treatment of estrogen dependent disorders such as, for example, breast cancer, endometriosis, endometrial cancer, polycystic ovarian disease, benign breast disease, gynecomastia, leyomyoma and the like.

The beneficial effect of aromatase inhibitors and/or antiestrogens in these disorders, especially in the treatment of breast cancer, is described in e.g. Cancer Research, 42, Suppl. 8:3261s(1982).

The anti-tumour activity of the present compounds of formula (I), especially in estrogen-dependent tumours, may be demonstrated in vivo, for example, by their effect on DMBA induced Mamma tumours in female Sprague-Dawley-rats.

In view of the usefulness of the subject compounds in the treatment of estrogen dependent disorders it is evident that the present invention provides a method of treating mammals suffering from said estrogen dependent disorder. Said method comprises the systemic administration to said mammals of an amount, effective to treat estrogen dependent disorders, of a compound of formula (I), a pharmaceutically acceptable acidaddition salt, or a stereochemically isomeric form thereof. In particular there is provided a method of inhibiting estrogen synthesis in mammals which comprises the systemic administration to said mammals of an estrogen synthesis inhibitory amount, more particularly an aromatase inhibitory amount, of a compound of formula (I).

In addition to the above, some compounds of formula (I) show less hepatotoxicity than the related prior art compounds.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprise saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any mature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete unites suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills powder packets, wafers, injectable solutions or suspensions, teaspoonfuls, tablespoonfuls and the like, and segregated multiples thereof.

Those of skill in treating the estrogen dependent disorder could easily determine the effective amount from the test results presented hereinafter. In general it is contemplated that an effective amount would be from 0.0001 mg/kg to 10 mg/kg body weight, and more preferably from 0.001 mg/kg to 0.5 mg/kg body weight.

The following examples are intended to illustrate and not to limit the scope of the invention. Unless otherwise stated all parts therein are by weight.

EXPERIMENTAL PART

A. PREPARATION OF THE INTERMEDIATES

EXAMPLE 1 a) A solution of 250 parts of 1-bromo-3-bromomethylbenzene, 168.5 parts of N,N-dimethyl-4-[3-[(trimethylsilyl)oxy]propyl]-1H-imidazole-1-carboxamide and 869 parts of acetonitrile was refluxed for 18 hours. After cooling to 0° C., ammonia was bubbled through the reaction mixture for 5 min. The solvent was evaporated and the residue was stirred for 1 hour in 1700 ml of hydrochloric acid 1N. The mixture was extracted with ethyl acetate. The aqueous layer was basified with $Na_2CO_3$(sat.) and reextracted with ethyl acetate (5×450 parts). The combined extracts were washed with water, dried, filtered and evaporated, yielding 210 parts (100%) of 1-[(3-bromophenyl)methyl]-1H-imidazole-5-propanol (interm. 1).

b) To a solution of 442 parts of thionyl chloride in 2793 parts of dichloromethane there was added dropwise a solution of 209 parts of intermediate 1 in 93 parts of dichloromethane. After refluxing for 3 hours and subsequent cooling, the reaction mixture was evaporated. The residue was triturated with hexane and 1,1'-oxybisethane and was then partitioned between $NaHCO_3$(sat.) and dichloromethane. The dichloromethane layer was separated, dried, filtered and evaporated. The residue was purified by flash column chromatography (silica gel; $CH_3COOC_2H_5/CH_3OH/NH_4OH$ 90:5:5). The eluent of the desired fraction was evaporated, yielding 88.3 parts (39.6%) of 1-[(3-bromophenyl)methyl]-5-(3-chloropropyl)-1H-imidazole (interm. 2).

c) To a solution of 44.4 parts of N-(1-methylethyl)-2-propanamine in 890 parts of tetrahydrofuran there were added 108.8 parts of a solution of n.butyllithium in hexane 2.5M. After stirring for ½ hour and subsequent cooling to −78° C., the solution was added dropwise to a cooled (−78° C.) solution of 63 parts of intermediate 2,51 parts of N,N,N',N'-tetramethyl-1,2-ethanediamine and 783 parts of tetrahydrofuran. Stirring at −78° C. was continued for 3¼ hours and then there was added an excess of NH₄Cl (sat.). After warming to room temperature, the organic layer was separated and concentrated. Dichloromethane was added to the residue and the whole was washed with water (3×). The dichloromethane layer was dried, filtered and evaporated. The residue was converted into the nitrate salt in methanol by the addition of a mixture of 1,1'-oxybisethane and nitric acid (pH 3). The solvent was evaporated and the residue was triturated with 1,1'-oxybisethane, yielding 66 parts (97%) of 5-(3-bromophenyl)-5,6,7,8-tetrahydroimidazo[1,5-a]pyridine mononitrate (interm. 3).

d) To a stirred and cooled (−20° C.) amount of 344 parts of sulfuric acid there were added portionwise 66 parts of intermediate 3. After 2 hours, the mixture was cooled at −78° C. and then diluted with 187 parts of water. Next there were added portionwise 272 parts of NaOH 50%, keeping the temperature below 30° C. After basifying to pH 9 with Na₂CO₃ 10%(aq.), the mixture was filtered. The precipitate was washed with dichloromethane. The filtrate layers were separated and the aqueous layer was extracted with dichloromethane (4×). The combined extracts were washed with water, dried, filtered and evaporated, yielding 43 parts (70.2%) of 5-(3-bromo-4-nitrophenyl)-5,6,7,8-tetrahydroimidazol[1,5-a]pyridine (interm. 4).

e) 4.0 Parts of intermediate 4 were purified by column chromatography (silica gel; CH₃COOC₂H₅/CH₃OH/NH₄OH 95:2.5:2.5). The eluent of the desired fractions was evaporated and the residue was dissolved in dichloromethane. This solution was washed with water, dried, filtered and evaporated. The residue was converted into the nitrate salt in 2-propanol by the addition of a mixture of 1,1'-oxybisethane and nitric acid (pH 3). The salt was recrystallized from a mixture of 2-propanol and water, yielding 1.04 parts (21.7%) of 5-(3-bromo-4-nitrophenyl)-5,6,7,8-tetrahydroimidazol[1,5-a]pyridine mononitrate (interm. 5); mp. 175.9° C.

EXAMPLE 2 a) Through a stirred solution of 4.0 parts of intermediate 4 in 20.25 parts of 1-butanol there was bubbled methanamine for 5 min. The solution was heated at 120°–121° C. for 2½ hours, cooled to room temperature and poured into water. The aqueous layer was separated and extracted with ethyl acetate. The combined organic layers were dried, filtered and evaporated. The residue was triturated with 1,1'-oxybisethane, yielding 3.1 parts (91.8%) of N-methyl-2-nitro-5-(5,6,7,8-tetrahydroimidazol[1,5-a]pyridin-5-yl)benzenamine (interm.6). In a similar manner there were also prepared:

TABLE 1

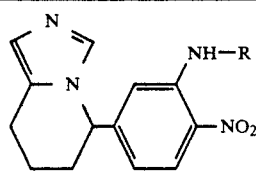

| Int. No. | R |
| --- | --- |
| 7 | —C₄H₉ |
| 8 | —CH(CH₃)₂ |
| 9 | —C₂H₅ |
| 10 | —(CH₂)₅—CH₃ |
| 11 | —(CH₂)₈—CH₃ |

TABLE 1-continued

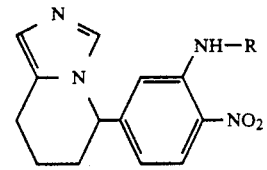

| Int. No. | R |
| --- | --- |
| 12 | —CH₂—C₆H₅ |
| 13 | -c-C₅H₉ |
| 14 | -n-C₃H₇ |
| 15 | —C(CH₃)₃ |
| 16 | —CH₂—CH(CH₃)₂ |
| 17. | —CH(CH₃)C₂H₅ |
| 18 | -c-C₆H₁₁ |
| 19 | —CH₂—CH=CH₂ | b) A solution of 3.0 parts of intermediate 6 in 79 parts of methanol was hydrogenated for 2¼ hours at 3.8 10⁵ Pa and at room temperature with a catalytic amount of Raney nickel. The catalyst was filtered off over diatomaceous earth and the filtrate was evaporated. The residue was purified by column chromatography (silica gel; CH₃COOC₂H₅/CH₃OH/NH₄OH 90:5:5). The eluent of the desired fraction was evaporated, yielding 1.6 parts (60.0%) of N²-methyl-4-(5,6,7,8-tetrahydroimidazol[1,5-a]pyridin-5-yl)-1,2-benzenediamine (interm. 20).

In a similar manner there were also prepared:

TABLE 2

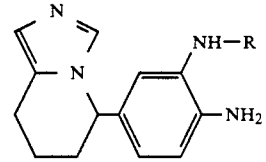

| Int. No. | R |
| --- | --- |
| 21 | —C₄H₉ |
| 22 | —CH(CH₃)₂ |
| 23 | —C₂H₅ |
| 24 | —(CH₂)₅—CH₃ |
| 25 | —(CH₂)₈—CH₃ |
| 26 | —CH₂—C₆H₅ |
| 27 | -c-C₅H₉ |
| 28 | -n-C₃H₇ |
| 29 | —C(CH₃)₃ |
| 30 | —CH₂—CH(CH₃)₂ |
| 31 | —CH(CH₃)C₂H₅ |
| 32 | -c-C₆H₁₁ |

EXAMPLE 3

To a cooled (0° C.) and stirred amount of 920 parts of sulfuric acid there were added portionwise 88.8 parts of 5-(4-bromophenyl)-5,6,7,8-tetrahydroimidazo[3,4-a]pyridine mononitrate. After stirring for 2 hours at 0° C., the reaction mixture was poured into 1000 parts of crushed ice. The whole was neutralized with a solution of 749 parts of sodium hydroxide in 810 parts of water while the temperature was kept below 35° C. After basifying to pH 8 with Na₂CO₃ (aq.), the product was extracted with dichloromethane (4×665 parts). The combined extracts were washed with water, dried, filtered and evaporated. The residue was purified twice by column chromatography (silica gel; CH₃COOC₂H₅/CH₃OH/NH₄OH 96:2:2). The eluent of the desired fraction was evaporated and the residue was dissolved in a mixture of methanol and 1,1'-oxybisethane. The nitrate salt was formed by the addition of a mixture of 1,1'-oxybisethane and nitric acid to pH 6. The salt was recrystallized from a mixture of 2-propanol and water, yielding 19.96 parts (25.9%) of 5-(4-bromo-3-nitrophenyl)-5,6,7,8-tetrahydroimidazo[3,4-a]pyridine mononitrate (interm. 33); mp. 170.8° C.

EXAMPLE 4

To a refluxing solution of 1.1 parts of intermediate 19 in 19.75 parts of ethanol there was added a solution of 3.9 parts of sodium dithionate in 20 parts of water. Refluxing was continued for 20 min. The ethanol was evaporated and the aqueous layer was extracted with dichloromethane (4×66.5 parts). The combined extracts were washed with water, dried, filtered and evaporated, yielding 0.71 parts (71.5%) of $N^2$-(2-propenyl)-4-(5,6,7,8-tetrahydroimidazo[1,5-a]pyridin-5-yl)-1,2-benzenediamine (interm. 34).

EXAMPLE 5 a) To a stirred and cooled (−10° C.) amount of 180 parts of sulfuric acid there were added portionwise 24.0 parts of 5-(3-chlorophenyl)-6,7-dihydro-5H-pyrrolo[1,2-c]imidazole mononitrate (described in U.S. Pat. No. 4,617,307). Stirring at 0° to −10° C. was continued for 2 hours. After cooling to −78° C., the mixture was diluted with 100 parts of water and then neutralized with a solution of 141 parts of NaOH in 200 parts of water, keeping the temperature below 28° C. The whole was basified to pH 9 with an excess of $Na_2CO_3$ 10% and was filtered when reached room temperature. The precipitate was washed with dichloromethane and the filtrate layers were separated. The aqueous layer was diluted with 100 parts of water and the whole was re-extracted with dichloromethane (4×399 parts). The combined dichloromethane layers were washed with NaCl (sat.), dried, filtered and evaporated, yielding 17.1 parts (75.9%) of 5-(3-chloro-4-nitrophenyl)-6,7-dihydro-5H-pyrrolo[1,2-c]imidazole (interm. 35).

b) Through a solution of 7.0 parts of intermediate 35 in 56.7 parts of 1-butanol there were bubbled 8.4 parts of methanamine in a pressure bottle. The bottle was closed and heated at 120°–122° C. for 6 hours while stirring. After cooling, there were added 27 parts of ethyl acetate. The whole was washed with water, dried, filtered and evaporated. The residue was purified by flash column chromatography (silica gel; $CH_3COOC_2H_5$/$CH_3OH$/$NH_4OH$ 95:2.5:2.5). The eluent of the desired fraction was evaporated, yielding 2.4 parts (34.4%) of 5-(6,7-dihydro-5H-pyrrolo[1,2-c]imidazol-5-yl)-N-methyl-2-nitrobenzenamine (interm. 36). In a similar manner there was also prepared N-butyl-5-(6,7-dihydro-5H-pyrrolo[1,2-c]-imidazol-5-yl)-2-nitrobenzenamine (interm. 37).

c) To a refluxing solution of 2.3 parts of hydrazine monohydrate, 23.7 parts of methanol and a small amount of Raney nickel, there was added a solution of 2.3 parts of intermediate 36 in 15.8 parts of methanol. After refluxing for 25 min. and consequent cooling, the reaction mixture was filtered over diatomaceous earth. The filtrate was evaporated, yielding 1.1 parts (54.1%) of 4-(6,7-dihydro-5H-pyrrolo[1,2-c]imidazol-5-yl)-$N^2$-methyl-1,2-benzenediamine (interm. 38). In a similar manner there was also prepared $N^2$-butyl-4-(6,7-dihydro-5H-pyrrolo[1,2-c]-imidazol-5-yl)-1,2-benzenediamine (interm. 39).

B. PREPARATION OF THE FINAL COMPOUNDS

EXAMPLE 6

To a stirred and cooled (0° C.) solution of 0.12 parts of intermediate 23 in 25 parts of HCl 5N there were added portionwise 0.29 parts of sodium nitrite while stirring. After stirring for 30 min. at 0° C., the reaction mixture was neutralized with NaOH 50% and then basified to pH 9 with $Na_2CO_3$ 10%. The whole was extracted with dichloromethane (5×32.5 parts) and the combined extracts were washed with water, dried, filtered and evaporated. The residue was purified by column chromatography (silica gel; $CH_3COOC_2H_5$/$CH_3OH$/$NH_4OH$ 95:2.5:2.5). The eluent of the desired fraction was evaporated and the residue was dissolved in dichloromethane. This solution was washed with water, dried, filtered and evaporated. The residue was converted into the hydrochloride salt in 2-propanol. The salt was triturated in 1,1'-oxybisethane and recrystallized from a mixture of 2-propanol and 1,1'-oxybisethane. The product was filtered off and dried in vacuo at 60° C. for 9 hours, yielding 0.37 parts (43.5%) of 1-ethyl-6-(5,6,7,8-tetrahydroimidazo[1,5-a]pyridin-5-yl)-1H-benzotriazole monohydrochloride; mp. 245.5° C. (compound 26).

EXAMPLE 7

A mixture of 10.0 parts of intermediate 33, 7.3 parts of hydrazine hydrate and 12 parts of 1-butanol was stirred for 18 hours at reflux temperature. After cooling, the reaction mixture was evaporated and the residue was taken up in 40 parts of methanol. The whole was filtered over diatomaceous earth and the filtrate was evaporated. The residue was purified by column chromatography (silica gel; $CH_3COOC_2H_5$/$CH_3OH$/$NH_4OH$ 70:25:5). The eluent of the desired fraction was evaporated and the residue was boiled in 25 parts of water, triturated in hot methanol (2x) and then suspended in a mixture of water and $NH_4OH$. The whole was filtered over diatomaceous earth and the filtrate was evaporated. The residue was dried in vacuo at 48° C. overnight, yielding 1.15 parts (16.1%) of 6-(5,6,7,8-tetrahydroimidazo[3,4-a]pyridin-5-yl)-1H-benzotriazol-1-ol; mp. 279.4° C. (compound 7).

EXAMPLE 8

To a stirred suspension of 0.60 parts of compound 7 and 1.9 parts of N,N-dimethylformamide there were added at once 0.55 parts of sodium carbonate. Stirring was continued for 5 hours at 52° C. under argon. After cooling, there was added dropwise a solution of 0.34 parts of (bromomethyl)cyclopropane and 0.19 parts of N,N-dimethylformamide. The whole was stirred for 4½ hours, treated with HCl and 1,1'-oxybisethane and was then evaporated. To the residue there were added 45 parts of water and $Na_2CO_3$ (sat.). The product was extracted with ethyl acetate (4×36 parts) and the combined extracts were washed with water, dried, filtered and evaporated. The residue was purified by column chromatography (silica gel; $CHCl_3$/$CH_3OH$ 95:5). The eluent of the desired fraction was evaporated and the residue was converted into the nitrate salt in 1,1'-oxybisethane. The salt was recrystallized from a mixture of methanol and 1,1'-oxybisethane, yielding 0.67 parts (71.1%) of 1-(cyclopropylmethoxy)-6-(5,6,7,8-tetrahydroimidazo[1,5-a]pyridin-5-yl)-1H -benzotriazole mononitrate; mp. 163.8° C. (compound 8).

EXAMPLE 9

To a stirred mixture of 1.50 parts of compound 7 in 28 parts of N,N-dimethylformamide there were added 1.44 parts of sodium carbonate under argon. Stirring was continued for ½ hour at 60° C. (oil-bath). Then there was added dropwise a solution of 0.74 parts of bromoacetonitrile in 5 parts of N,N-dimethylformamide. After stirring for ½ hour at 60° C. and for 3 hours at room temperature, the reaction mixture was evaporated and the residue was taken up in methanol. The whole was filtered and the filtrate was evaporated. The residue was purified by column chromatography (silica gel; $CH_3COOC_2H_5/CH_3OH/NH_4OH$ 70:25:5). The eluent of the desired fraction was evaporated and the residue was dissolved in dichloromethane. This solution was washed with water (2×), dried, filtered and evaporated. The residue was converted into the hydrochloride salt in 1,1'-oxybisethane. The salt was filtered off and dried in vacuo at 70° C. for 24 hours, yielding 1.04 parts (63.9%) of 6-(5,6,7,8-tetrahydroimidazo[1,5-a]pyridin-5-yl)-1H-benzotriazole monohydrochloride; mp. 278.0° C. (compound 17).

All the other compounds listed in table 3 were obtained by analogous methods of preparation as described in examples 6-9, the actual method of preparation being indicated in column 2 (Ex. No.).

TABLE 3

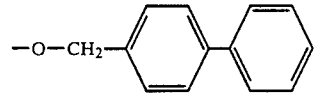

| Comp. No. | Ex. No. | $R^2$ | n | Physical data (salt/mp. °C.) |
|---|---|---|---|---|
| 1 | 8 | $-O-CH_2-C_6H_5$ | 1 | 127.9 |
| 2 | 8 | $-O-CH_2-(4-CN-C_6H_4)$ | 1 | 146.9 |
| 3 | 8 | $-O-CH_2-CH_2-CH_3$ | 1 | HCl/198.4 |
| 4 | 8 | $-O-CH_2-CH_3$ | 1 | HCl/½H$_2$O/182.1 |
| 5 | 8 | $-O-CH_2-CH=CH_2$ | 1 | HCl/177.5 |
| 6 | 8 | $-O-CH_2-CH(CH_3)_2$ | 1 | HCl/196.2 |
| 7 | 7 | $-OH$ | 1 | 279.4 |
| 8 | 8 | $-O-CH_2$-c-$C_3H_5$ | 1 | HNO$_3$/163.8 |
| 9 | 8 | $-O-CH_3$ | 1 | HNO$_3$/166.1 |
| 10 | 8 | $-O-(CH_2)_3-CH_3$ | 1 | HNO$_3$/154.2 |
| 11 | 8 | $-O-(CH_2)_7-CH_3$ | 1 | HI/158.8 |
| 12 | 8 | $-O-CH_2-C(=CH_2)CH_3$ | 1 | HCl/179.9 |
| 13 | 8 | $-O-CH_2-CH=C(CH_3)_2$ | 1 | HCl/159.6 |
| 14 | 8 | $-O-CH_2-C\equiv CH$ | 1 | HCl/178.1 |
| 15 | 8 | $-O-(CH_2)_4-COOC_2H_5$ | 1 | HCl/125.5 |
| 16 | 8 | $-O-CH(CH_3)_2$ | 1 | HCl/204.6 |
| 17 | 9 | $-H$ | 1 | HCl/278.0 |
| 18 | 8 | $-O-(CH_2)_4-CN$ | 1 | HNO$_3$/160.8 |
| 19 | 8 | 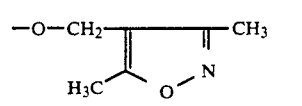 | 1 | HCl/137.3 |
| 20 | 8 | $-O-CH(CH_3)-C_2H_5$ | 1 | HNO$_3$/164.2 |
| 21 | 8 | $-O-(CH_2)_2-OH$ | 1 | ½fumarate/170.1 |
| 22 | 8 | $-O-CH_2-$ (isoxazole with CH$_3$, H$_3$C substituents) | 1 | HCl/H2O/139.7 |
| 23 | 6 | $-CH_3$ | 1 | HCl/H$_2$O/161.3 |
| 24 | 6 | $-(CH_2)_3-CH_3$ | 1 | HCl/228.5 |
| 25 | 6 | $-CH(CH_3)_2$ | 1 | HCl/229.9 |
| 26 | 6 | $-C_2H_5$ | 1 | HCl/245.5 |
| 27 | 6 | $-(CH_2)_5-CH_3$ | 1 | HCl/125.1 |
| 28 | 6 | $-(CH_2)_8-CH_3$ | 1 | HCl/½H$_2$O/137.5 |
| 29 | 6 | $-CH_2-C_6H_5$ | 1 | HCl/231.1 |
| 30 | 6 | -c-C$_5$H$_9$ | 1 | HCl/205.1 |
| 31 | 6 | -n-C$_3$H$_7$ | 1 | HCl/½H$_2$O/184.5 |
| 32 | 6 | -t-C$_4$H$_9$ | 1 | ½(CH$_3$)$_2$CHOH/HCl/169.4 |
| 33 | 6 | $-CH_2-CH(CH_3)_2$ | 1 | HCl/200.5 |
| 34 | 6 | $-CH(CH_3)C_2H_5$ | 1 | HCl/$\frac{3}{2}$H$_2$O/115.8 |
| 35 | 6 | -c-C$_6$H$_{11}$ | 1 | HCl/201.5 |
| 36 | 8 | $-O-(CH_2)_7-COOCH_3$ | 1 | HNO$_3$/123.7 |
| 37 | 8 | $-O-(CH_2)_2-CONH_2$ | 1 | fumarate/152.4 |

TABLE 3-continued

| Comp. No. | Ex. No. | R² | n | Physical data (salt/mp. °C.) |
|---|---|---|---|---|
| 38 | 6 | —CH₂—CH=CH₂ | 1 | HCl/215.1 |
| 39 | 6 | —(CH₂)₃—CH₃ | 0 | HCl/216.7 |
| 40 | 6 | —CH₃ | 0 | fumarate/182.2 |

C. PHARMACOLOGICAL EXAMPLES

The useful inhibition of the aromatase activity of the compounds of formula (I) can be demonstrated in the following test procedures.

EXAMPLE 10

In Vitro-Inhibition of the Aromatase Activity Test

The effect of the compounds of the present invention on the conversion of 1,2[3H]androstenedione into estrone and estradiol was studied in the presence of human placental microsomes following procedures analogous to those described in J. Steroid Biochem., 7, 787 (1976).

Human placental microsomes were diluted in potassium phosphate buffer (0.1M, pH 7.4) to give about 50% conversion of androgens to estrogens (protein content: about 0.5 mg). Four ml human placental microsomes were incubated in a final volume of 5 ml with 0.2 µCi 1,2[³H]-androstenedione, 2 µg and androstenedione and 5 µl of test compoun and/or dimethylsulfoxide (DMSO). Further the incubation mixture contained a NADPH-regenerating system consisting of ATP (2,48 mM), NADP (0.97 mM), glucose-6-phosphate (8.22 mM), glucose-6-phosphate dehydrogenase (0.98 units) and MgCl₂ (2.46 mM). The reaction was initiated by the addition of androstenedione and proceeded for 30 min at 37° C. During the incubation period, the mixtures were gassed with air. In this assay, aromatization of androstenedione results in the production of [3H]-H₂O which is isolated by extracting the samples with chloroform to remove the free steroid. Samples are counted in a liquid scintillation spectrometer and the percent inhibition is determined by comparing the results with control samples incubated without inhibitor. The effects of the compounds of the present invention are presented in table 4, as the concentration in µM of the compound required to obtain 50% inhibition of the estrogen synthesis (IC₅₀-values).

EXAMPLE 11

In Vivo-Inhibition of the Aromatase Activity

Immature female Wistar rats weighing 120 g were injected subcutaneously with 200 I.U. of pregnant mare's serum gonadotropin (PMSG). Ninety hours later, 1 mg/kg of the test compound dissolved in 0.5 ml 20% polyethyleneglycol in water was administered by oral gavage. Control animals received 20% polyethyleneglycol only. Two hours following drug or placebo administration the rats were killed by decapitation and trunk blood was collected on heparine. Plasma estradiol concentrations were measured by standard radio-immunological procedures. The percentage recovered estradiol relative to the untreated controls is depicted in the last column of table 4. The results in this table are not given for the purpose of limiting the invention thereto but only to exemplify the useful pharmacological properties of all the compounds within the scope of formula (I).

TABLE 4

| Comp. No. | Aromatase in vitro IC₅₀ in µM | Aromatase in vivo % inhibition at 1 mg/kg |
|---|---|---|
| 2 | 0.0442 | 96 |
| 3 | 0.0295 | 92 |
| 4 | 0.0375 | 94 |
| 5 | 0.0279 | 95 |
| 6 | 0.0592 | 86 |
| 8 | 0.0319 | 87 |
| 9 | 0.0570 | 89 |
| 10 | 0.0317 | 88 |
| 12 | 0.0252 | 85 |
| 14 | 0.0295 | 80 |
| 18 | 0.0346 | 88 |
| 20 | 0.0393 | 87 |
| 21 | <1.0000 | 88 |
| 23 | 0.0898 | 93 |
| 24 | 0.0317 | 89 |
| 25 | 0.0556 | 91 |
| 26 | 0.0540 | 93 |
| 27 | 0.0254 | 86 |
| 30 | 0.0423 | 93 |
| 31 | 0.0435 | 96 |
| 32 | 0.054 | 95 |
| 33 | 0.046 | 96 |
| 35 | 0.041 | 98 |

D. Composition Examples

The following formulations exemplify typical pharmaceutical compositions in dosage unit form suitable for systemic administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

EXAMPLE 12

Oral drops 500 g of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg/ml of the A.I. The resulting solution was filled into suitable containers.

EXAMPLE 13

Oral solutions 9 g of methyl 4-hydroxybenzoate and 1 g of propyl 4-hydroxybenzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propanetriol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the A.I. per teaspoonful (5 ml). The resulting solution was filled in suitable containers.

EXAMPLE 14

Capsules 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 20 mg of the A.I.

EXAMPLE 15

Film-coated tablets

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each comprising 10 mg of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated colour suspension (Opaspray K-1-2109 ®) and the whole was homogenated. The tablet cores were coated with the thus obtained mixture in a coating apparatus.

EXAMPLE 16

Injectable solutions 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I.. The solution was cooled to room temperature and supplemented with water for injection q.s. ad 1 l volume, giving a solution of 4 mg A.I. per ml. The solution was sterilized by filtration (U.S.P. XVII p. 811) and filled in sterile containers.

EXAMPLE 17

Suppositories 3 g A.I. was dissolved in a solution of 3 g 2,3-dihydroxybutanedioic acid in 25 ml polyethylene glycol 400. 12 g surfactant (SPAN ®) and triglycerides (Witepsol 555 ®) q.s. ad 300 g were molten together. The latter mixture was mixed well with the former solution. The thus obtained mixture was poured into moulds at a temperature of 37°-38° C. to form 100 suppositories each containing 30 mg of the A.I.

We claim:

1. A compound having the formula

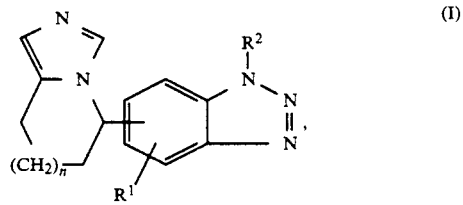

(I)

a pharmaceutically acceptable acid addition salt thereof or a stereochemically isomeric form thereof, wherein
n is 0 or 1;
$R^1$ is hydrogen, nitro, amino, mono- or di($C_{1-6}$alkyl)amino, halo, $C_{1-6}$alkyl, hydroxy or $C_{1-6}$alkyloxy;
$R^2$ is hydrogen; $C_{1-10}$alkyl; $C_{3-6}$alkenyl; $C_{3-6}$alkynyl; $C_{3-7}$cycloalkyl; bicyclo[2.2.1]heptan-2-yl; 2,3-dihydro-1H-indenyl; 1,2,3,4-tetrahydronaphthalenyl; phenyl; substituted phenyl; $C_{1-10}$alkyl substituted with phenyl, substituted phenyl, naphthalenyl, thienyl, furanyl, $C_{1-4}$alkylfuranyl, $C_{3-7}$cycloalkyl, hydroxy or with $C_{1-6}$alkyloxy; or a radical of formula —$OR^3$;
$R^3$ is hydrogen; $C_{1-10}$alkyl; $C_{3-6}$alkenyl; phenyl$C_{3-6}$alkenyl; $C_{3-6}$alkynyl; pyrimidinyl; diphenylmethyl; 1-$C_{1-4}$alkylpiperidin-4-yl; $C_{1-10}$alkyl substituted with halo, hydroxy, $C_{1-6}$alkyloxy, amino, mono- or di($C_{1-6}$alkyl)amino, trifluoromethyl, cyano, aminocarbonyl, hydroxycarbonyl, $C_{1-6}$alkyloxycarbonyl, phenyl, substituted phenyl, thienyl, furanyl, $C_{1-4}$alkylfuranyl, pyridinyl, di($C_{1-6}$alkyl)isoxazolyl, phenoxy, phenylthio, $C_{3-7}$cycloalkyl, 2,3-dihydro-1,4-benzodioxinyl, 1H-benzimidazolyl, $C_{1-4}$alkyl substituted 1H-benzimidazolyl, (1,1'-biphenyl)-4-yl or 2,3-dihydro-2-oxo-1H-benzimidazolyl; and
each substituted phenyl independently is phenyl substituted with from 1 to 3 substituents independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro.

2. A compound according to claim 1 wherein the 5,6,7,8-tetrahydroimidazo[1,5-a]pyridin-5-yl or the 6,7-dihydro-5H-pyrrolo[1,2-c]imidazol-5yl moiety is substituted on either the 5 or the 6 position of the benzotriazole moiety.

3. A compound according to claim 1 wherein n is 1; $R^1$ is hydrogen; $R^2$ is hydrogen, $C_{1-6}$alkyl, $C_{3-6}$alkenyl, $C_{3-6}$alkynyl, $C_{3-7}$cycloalkyl, phenyl, substituted phenyl, bicyclo[2.2.1]heptan-2-yl, 2,3-dihydro-1H-indenyl, 1,2,3,4-tetrahydronaphthalenyl, $C_{1-6}$alkyl substituted with phenyl, substituted phenyl, naphthalenyl, thienyl, furanyl, $C_{1-4}$alkylfuranyl, $C_{3-7}$cycloalkyl, hydroxy, $C_{1-4}$alkyloxy or a radical —OR$^3$; and; R$^3$ is hydrogen, $C_{1-6}$alkyl, $C_{3-6}$alkenyl, phenyl$C_{3-6}$alkenyl; $C_{3-6}$alkynyl; pyrimidinyl; diphenylmethyl, (1-$C_{1-4}$alkyl-4piperidinyl); $C_{1-6}$alkyl substituted with halo, hydroxy, amino, mono- or di($C_{1-6}$alkyl)amino, trifluoromethyl, cyano, aminocarbonyl, hydroxycarbonyl, $C_{1-6}$alkyloxycarbonyl, phenyl, substituted phenyl, thienyl, furanyl, $C_{1-4}$alkylfuranyl, pyridinyl, di($C_{1-6}$alkyl)isoxazolyl, phenoxy, phenylthio, $C_{3-7}$cycloalkyl, 2,3-dihydro-1,4-benzodioxinyl, 1H-benzimidazolyl, $C_{1-4}$alkyl substituted 1H-benzimidazolyl, (1,1'-biphenyl)-4-yl or 2,3-dihydro-2-oxo-1H-benzimidazolyl.

4. A compound according to claim 1 wherein n is 0; R$^1$ is hydrogen; R$^2$ is hydrogen, $C_{1-6}$alkyl, $C_{3-7}$cycloalkyl, $C_{1-6}$alkyl substituted with $C_{3-7}$cycloalkyl or a radical —OR$^3$; R$^3$ is hydrogen or $C_{1-6}$alkyl.

5. A compound according to claim 3 wherein R$^2$ is $C_{1-6}$alkyl optionally substituted with $C_{3-7}$cycloalkyl; $C_{3-7}$cycloalkyl; bicyclo[2.2.1]heptan-2-yl; 2,3-dihydro-1H-indenyl; 1,2,3,4-tetrahydronaphthalenyl; or a radical —OR$^3$; and
R$^3$ is $C_{1-6}$alkyl optionally substituted with hydroxy, cyano, phenyl, substituted phenyl, $C_{3-7}$cycloalkyl; or $C_{3-6}$alkenyl.

6. A compound according to claim 5 wherein R$^2$ is $C_{1-4}$alkyl.

7. A compound according to claim 6 wherein the compound is 1-ethyl-6-(5,6,7,8-tetrahydroimidazo[1,5-a]pyridin-5-yl)-1H-benzotriazole monohydrochloride.

8. A pharmaceutical composition comprising an inert carrier and as active ingredient an estrogen hormone biosynthesis inhibiting amount of a compound as claimed in any one of claims 1-7.

9. A method of treating mammals suffering from estrogen dependent disorders, said method comprising the systemic administration to said mammals of an effective amount to treat estrogen dependent disorders of a compound as claimed in any one of claims 1-7.

* * * * *